(12) United States Patent
Li (10) Patent No.: US 11,998,664 B2
(45) Date of Patent: Jun. 4, 2024

(54) URETERAL STENT AND MANUFACTURE METHOD THEREFOR

(71) Applicant: Jiangsu Biosurf Biotech co., Ltd., Jiangsu (CN)

(72) Inventor: Ye Li, Jiangsu (CN)

(73) Assignee: Jiangsu Biosurf Biotech co., Ltd, Jiangsu (CN)

( * ) Notice: Subject to any disclaimer, the term of this patent is extended or adjusted under 35 U.S.C. 154(b) by 556 days.

(21) Appl. No.: 17/427,739

(22) PCT Filed: Nov. 11, 2019

(86) PCT No.: PCT/CN2019/117154
§ 371 (c)(1),
(2) Date: Aug. 2, 2021

(87) PCT Pub. No.: WO2020/155746
PCT Pub. Date: Aug. 6, 2020

(65) Prior Publication Data
US 2022/0062511 A1 Mar. 3, 2022

(30) Foreign Application Priority Data
Feb. 2, 2019 (CN) .......................... 201910107526.2

(51) Int. Cl.
*A61L 31/10* (2006.01)
*A61L 31/14* (2006.01)
(Continued)

(52) U.S. Cl.
CPC ............... *A61L 31/10* (2013.01); *A61L 31/14* (2013.01); *C10M 107/42* (2013.01);
(Continued)

(58) Field of Classification Search
CPC ...... A61L 31/10; A61L 31/14; A61L 2400/10; A61L 2420/08; A61L 2420/06;
(Continued)

(56) References Cited

U.S. PATENT DOCUMENTS 6,794,425 B1 9/2004 Ellis et al.
8,080,096 B2 * 12/2011 Yamashita ............... G03G 8/00
106/31.08

(Continued)

FOREIGN PATENT DOCUMENTS

CN 101959914 A 1/2011
CN 104558666 A 4/2015
(Continued)

OTHER PUBLICATIONS

International Search Report mailed Aug. 6, 2020 in related PCT Application No. PCT/CN2019/117154, 8 pages.

*Primary Examiner* — Liam J Heincer
*Assistant Examiner* — Zhen Liu
(74) *Attorney, Agent, or Firm* — Fox Rothschild LLP (57) ABSTRACT

The present disclosure relates to a ureteral stent and a preparation method thereof. The ureteral stent has at least one pre-coating formed on its surface and at least one hydrophilic lubricating coating formed on the pre-coating. Preferably, the pre-coating and the hydrophilic lubricating coating are formed by photocuring, thermal curing, chemical reaction, physical adsorption, crystallization or freezing. By means of the technical solutions of the present disclosure, a stable and firm coating is formed on the surface of the ureteral stent with a more complicated shape, the friction force (the friction force of the $30^{th}$ cycle is small, and the friction force of the $30^{th}$ cycle/initial friction force is kept within 2 times) of the ureteral stent is greatly reduced, and the lubricating performance is greatly improved.

20 Claims, 2 Drawing Sheets

(51) Int. Cl.
   *C10M 107/42* (2006.01)
   *C10M 107/44* (2006.01)
   *C10N 40/00* (2006.01)
   *C10N 50/00* (2006.01)

(52) U.S. Cl.
   CPC ........ *C10M 107/44* (2013.01); *A61L 2400/10* (2013.01); *A61L 2420/08* (2013.01); *C10M 2217/0235* (2013.01); *C10M 2217/0453* (2013.01); *C10N 2040/50* (2020.05); *C10N 2050/023* (2020.05)

(58) Field of Classification Search
   CPC .............. C10M 107/42; C10M 107/44; C10M 2217/0235; C10M 2217/0453; C10N 2040/50; C10N 2050/023
   See application file for complete search history.

(56) References Cited

U.S. PATENT DOCUMENTS

| | | | |
|---|---|---|---|
| 10,802,401 B2 * | 10/2020 | Tanigaki | ................. G03F 7/105 |
| 2010/0049146 A1 * | 2/2010 | Nielsen | .................... C08J 7/123 |
| | | | 427/2.3 |
| 2010/0273939 A1 | 10/2010 | Stollmaier et al. | |
| 2013/0053470 A1 | 2/2013 | Raisin-Dadre et al. | |

FOREIGN PATENT DOCUMENTS

| | | |
|---|---|---|
| CN | 104927024 A | 9/2015 |
| CN | 102908712 B | 3/2016 |
| CN | 105983138 A | 10/2016 |
| CN | 105983139 A | 10/2016 |
| CN | 105985721 A | 10/2016 |
| CN | 207401003 U | 5/2018 |
| CN | 108815586 A | 11/2018 |

* cited by examiner

URETERAL STENT AND MANUFACTURE METHOD THEREFOR

This application is a U.S. national stage application of the PCT International Application No. PCT/CN2019/117154 filed on Nov. 11, 2019, which claims the benefit of foreign priority of Chinese patent application No. 201910107526.2 filed on Feb. 2, 2019, the contents all of which are incorporated herein by reference in their entireties.

TECHNICAL FIELD

The present disclosure belongs to the field of medical devices, and specifically relates to the field of ureteral stents with pre-coatings and hydrophilic lubricating coatings.

BACKGROUND

A ureteral stent is widely used in urological surgeries, and is suitable for the above-mentioned urinary tract surgeries such as kidney stones, ureteral calculus, hydronephrosis, kidney transplantation, benign tumors of the kidney and ureter, as well as treatment processes such as lithotripsy of lithotriptors, dilatation of ureterostenosis. After being implanted in the ureter, the ureteral stent can drain urine and prevent ureteral stricture and adhesion blockage. When in use, one end of the ureteral stent is placed in the renal pelvis, the stent body is placed in the ureter, and the other end is placed in the bladder. The existing ureteral stent is usually made of medical polymer materials, such as silicone rubber or polyurethane. The tail ends of a tube are opposite to each other and are bend inward into a circle, shaped like a pig tail, therefore, the ureteral stent is also called a pig tail tube or double "J" tube. Since the ureteral stent must be placed and removed through invasive operations, although this type of operations is not a major operation, a patient will be painful. What is more serious is that urinary tract tissues will be damaged to varying degrees when the tube is placed or removed. After being placed, the ureteral stent is routinely left in the body of the patient for a certain period of time, often accompanied by some complications. Therefore, it is necessary to perform long-acting lubrication treatment on the surface of the ureteral stent to reduce complications and relieve the suffering of the patient.

The surface functionalization treatment method of the ureteral stent is usually a physical method, for example, directly soaking a lubricating layer or depositing plasma on the surface of the material. However, due to the relatively complex structure of the ureteral stent, a functionalized coating obtained by the above method has poor firmness and flatness. Therefore, there is a need for a method that can form a long-lasting firm and uniform lubricating coating on the surface of the ureteral stent.

CN 102908712 B discloses a ureteral stent, which includes an antibacterial layer and a lubricating layer, which are formed on the outer side of a body from the inside out. The coating is prepared by immersing the body in a solution of functional molecules (hydrophilic or antibacterial), then taking out the body, and removing the seal to obtain a functionalized ureteral stent. In this method, functional molecules are adsorbed on the surface of the ureteral stent by soaking, but the coating on the surface is easy to fall off and is easy to remain in vivo, thus causing potential safety hazards.

CN 207401003 U discloses a ureteral stent, a layer of fluorocarbon nano-polymer hydrophobic coating is formed on the surface through the plasma coating technology, and a protective film is formed on the inner and outer surfaces of the ureteral stent to separate body fluid and urine from the surface of the ureteral stent, thereby preventing the direct contact with the body fluid and the urine. The preparation method is simple, but the obtained coating contains the fluorocarbon nano-polymer, the shedding of nanoparticles in the weak coating will affect the subsequent use, and a relatively consistent view is that hydrophilic materials have better biocompatibility than hydrophobic materials.

CN 108815586 A discloses a method for preparing a biological antifouling coating with long-lasting superhydrophilic properties. Multiple hydrophilic functional groups are generated on the surface of the coating by adding a polyphenol compound, a polyamine compound and a water-soluble oxidant. However, there is a risk of precipitation of small molecule oxidants, which increases the risk in the long-term use of modified medical devices.

SUMMARY

Problems to be Solved by the Disclosure

In order to solve the above shortcomings and deficiencies of the prior art, the present disclosure provides a ureteral stent with a long-lasting hydrophilic lubricating coating, which has good lubricating performance, excellent biological safety and high surface coating firmness, and the coating is uniform.

Solutions to the Problems

The present disclosure provides a ureteral stent. The ureteral stent has at least one pre-coating formed on its surface and at least one hydrophilic lubricating coating formed on the pre-coating,
  the pre-coating is formed by a pre-coated coating composition, the pre-coated coating composition includes photocurable polyurethane, a polymerizable hydrophilic polymer and a solvent, the main chain of the photocurable polyurethane contains a tertiary amine group, the side chain thereof has an unsaturated double bond group and a photosensitive group unit, and the side chain of the polymerizable hydrophilic polymer has an unsaturated double bond group; and
  the hydrophilic lubricating coating is formed by a hydrophilic lubricating coating composition, the hydrophilic lubricating coating composition includes a photocurable polymer, the photocurable polymer is copolymerized by a water-soluble polymerizable photosensitive monomer and a hydrophilic monomer, the water-soluble polymerizable photosensitive monomer contains: 1) a unit containing a photosensitive structure; 2) a unit containing a quaternary ammonium salt structure; and 3) a unit containing an unsaturated bond structure; and the unit containing a photosensitive structure is connected to the unit containing a quaternary ammonium salt structure at least through —C(=O)—, and the unit containing an unsaturated bond structure is connected to the unit containing a photosensitive structure through the unit containing a quaternary ammonium salt structure.

According to the ureteral stent of the present disclosure, the mass concentration of the photocurable polyurethane in the pre-coated coating composition is 0.1-50%, preferably, the range of the mass concentration is 0.5-30%, and more preferably, the range of the mass concentration is 20-30%; and the mass concentration of the polymerizable hydrophilic polymer in the pre-coated coating composition is 0.1-30%, and preferably, the range of the mass concentration is 1-20%; and
  the mass concentration of the photocurable polymer in the hydrophilic lubricating coating composition is 0.5-10%, preferably, the mass concentration is 2.5-7.5%, and more preferably 5%.

According to the ureteral stent of the present disclosure, the solvent is a solvent that can dissolve the photocurable polyurethane to form a homogeneous solution, and is preferably one or more of water, low molecular weight alcohol, ethyl acetate, n-hexane, dichloromethane, trichloromethane, N,N-dimethylformamide, N,N-dimethylacetamide, dimethyl sulfoxide, acetone, ether, toluene, benzene, xylene, cyclohexane and phenol.

According to the ureteral stent of the present disclosure, the photocurable polyurethane is obtained at least by the reaction of a polypolyol, an unsaturated polyol containing a tertiary amine group, a polyol containing a benzophenone group, and isocyanate.

According to the ureteral stent of the present disclosure, the structural formula of the photocurable polyurethane is as follows:

R represents the residue of polyol;
$R_1$ represents the residue of diisocyanate;
$R_2$ represents $-(CH_2)_p-$, p=1-4;
$R_3$ represents $-(CH_2)_q-$, q=1-3;
$R_4$ represents O or NH; $R_5$ represents H or $CH_3$; and
m, n, e, and f represent the number of repetitive units, and they are all integers not equal to zero.

According to the ureteral stent of the present disclosure, the structural formula of the polymerizable hydrophilic polymer is as follows:

wherein, $R_6$, $R_7$ and $R_8$ represent H or $CH_3$, g and h represent the number of repetitive units and both are integers not equal to 0, and i represents an integer of 1-4.

According to the ureteral stent of the present disclosure, the water-soluble polymerizable photosensitive monomer has a structure of general formula (I):

wherein: $R_1$=$CH_3$ or H; $R_2$ and $R_3$ are independently selected from linear alkyls having 1 to 20 C atoms or branched alkyls having 3 to 20 C atoms, respectively; X represents halogen; n=1-10; m=1-4; f=1-3; preferably, $R_2$ and $R_3$ are the same, X represents bromine, n=1, m=1, and f=1; and more preferably, $R_2$ and $R_3$ are both methyl or ethyl, X represents bromine, n=1, m=1, and f=1.

According to the ureteral stent of the present disclosure, the hydrophilic monomer includes one or more of unsaturated carboxylic acid or carboxylate, unsaturated carboxylic ester, unsaturated acid hydroxyalkyl ester, unsaturated anhydride, unsaturated amide, unsaturated lactam and epoxyalkane; preferably, the hydrophilic monomer includes one or more of (meth) acrylic acid, (meth) acrylamide, vinyl pyrrolidone, (meth) acrylate hydroxyethyl (propyl) ester, vinyl acetate, ethylene oxide, maleic acid, maleic anhydride, fumaric acid, fumaric anhydride and dimethylacrylamide; and more preferably, the hydrophilic monomer is selected from vinyl pyrrolidone.

According to the ureteral stent of the present disclosure, the molar concentration of the water-soluble polymerizable photosensitive monomer in the photocurable polymer is 0.08-12%, preferably 0.5-8%, further preferably 3-7.5%, more preferably 3-5%, and most preferably 4%.

The present disclosure further provides a preparation method of the ureteral stent according to the present disclosure, wherein at least one pre-coating is formed on the surface of the ureteral stent, then at least one hydrophilic lubricating coating is formed on the pre-coating, and preferably, the pre-coating and the hydrophilic lubricating coating are formed by photocuring, thermal curing, chemical reaction, physical adsorption, crystallization or freezing.

Effect of the Disclosure

The present disclosure uses a coating composition containing the photocurable polyurethane and the polymerizable hydrophilic polymer as the pre-coating, which can help to obtain a stable and firm functional coating on the ureteral stent. The side chain of polyurethane has the unsaturated double bond group and the photosensitive group unit, which can perform photo-initiated polymerization, and the main chain contains the tertiary amine group, which can be used as a photoinitiator to improve the photoinitiation efficiency. Polyurethane has a greater adhesion force, so that the coating firmness of the functional coating on the substrate can be improved. The hydrophilic polymer exposed on the outer surface of the pre-coating has better stretchability in the subsequently coated aqueous masking liquid, and the residual unsaturated double bonds can participate in the subsequent polymerization and curing of the hydrophilic lubricating coating, thereby enhancing the adhesion force of the hydrophilic lubricating coating between the substrates. By curing the coating composition, the pre-coating with high firmness, excellent biological safety and compatibility can be obtained. By adjusting the structure of the photocurable polyurethane molecules and the hydrophilic polymer and the concentration in the solution, the performance of the coating can be optimized. Combined with the subsequent hydrophilic lubricating coating, the firm and stable composite functional coating can be formed on the surface of the ureteral stent.

In addition, in the present disclosure, the coating composition used for preparing the photocurable hydrophilic lubricating coating is formulated based on the photocurable polymer. Compared with other existing photocurable coatings, the photocurable polymer used in the present disclosure itself contains the photosensitive structure unit, so there is no need to add small molecule photoinitiators into the coating composition, thereby overcoming the problems of residue and migration of the small molecule photoinitiators in the coating, having excellent biological safety and compatibility, and being suitable for the medical field.

Therefore, compared with the prior art, the present disclosure has beneficial effects as follows:
(1) A pre-coating is formed on the surface of the ureteral stent having a more complicated shape by photocuring, and the pre-coating can improve the coating firmness of the lubricant coating on the substrate thereafter.
(2) After forming a pre-coating on the surface, the second layer of hydrophilic lubricating coating is relatively stable and firm, and is also relatively smooth and uniform.
(3) The present disclosure can obtain a hydrophilic lubricating coating with high lubricity, and after being rubbed repeatedly for 30 times in a simulated human tissue environment, the coating does not fall off, the lubricity does not decrease, and the firmness of the coating is excellent.

DETAILED DESCRIPTION OF THE EMBODIMENTS

The technical solutions of the present disclosure will be described in detail below in conjunction with embodiments.

In the present disclosure, the term "monomer" means any chemical substance, which can be characterized by a chemical formula and has polymerizable groups (including (meth) acrylate groups) that can be polymerized into an oligomer or a polymer to increase the molecular weight. The molecular weight of the monomer can usually be calculated simply according to a given chemical formula.

Hereinafter, when a part of a molecule is described as "optionally substituted" or "substituted", this means that the part may be substituted with one or more substituents selected from $C_1$-$C_6$ linear chains, branched or cyclic alkyl, aryl, —OH, —CN, halogen, amine, amide, alcohol, ether, thioether, sulfone and derivatives thereof, sulfoxide and derivatives thereof, carbonic ester, isocyanate, nitrate and acrylate.

In the present disclosure, the meaning of the term "unit" not only includes functional groups (such as photosensitive groups, quaternary ammonium salt groups and unsaturated groups), but can also include additional chemical groups that have less influence on the functional groups, such as alkyl and alkylene.

In the present disclosure, the term "polymer" refers to a molecule containing two or more repetitive units. Specifically, the polymer can be formed by two or more identical or different monomers, and when used in the present disclosure, the term further includes oligomers or prepolymers. In the present disclosure, the term "molecular weight" refers to number-average molecular weight (Mn), and Mn is defined as Mn measured by light scattering (optionally in combination with size exclusion chromatography SEC).

In the present disclosure, the term "curing" is understood as: physical or chemical hardening or solidification caused by any method such as heating, cooling, drying and crystallization, or curing caused by a chemical reaction, such as radiation curing, thermal curing, or adding curing molecules and initiators for curing.

In the present disclosure, the term "photocuring" can be implemented in an exemplary manner as follows: a photoinitiation process is generated through light irradiation or UV irradiation with a wavelength ranging from 100 nm to 600 nm. Irradiation sources that can be used are sunlight or artificial lights or laser. For example, high-voltage, medium-voltage or low-voltage mercury lamps and xenon and tungsten lamps are advantageous. Likewise, excimer-based, solid-state and diode-based lasers are advantageous. A diode-based light source is generally beneficial to initiating chemical reactions.

<Ureteral Stent>

The present disclosure provides a ureteral stent. The ureteral stent has at least one pre-coating formed on its surface and at least one hydrophilic lubricating coating formed on the pre-coating.

<Pre-Coated Coating Composition>

In the present disclosure, the pre-coating is formed by a pre-coated coating composition, the pre-coated coating composition includes photocurable polyurethane, a polymerizable hydrophilic polymer and a solvent, the main chain of the photocurable polyurethane contains a tertiary amine group, the side chain thereof has an unsaturated double bond group and a photosensitive group unit, and the side chain of the polymerizable hydrophilic polymer has an unsaturated double bond group.

Photocurable Polyurethane

The photocurable polyurethane of the present disclosure is obtained by the reaction of multiple kinds of polyols and isocyanates, and the main chain of which contains the tertiary amine group, and the side chain thereof has the unsaturated double bond group and the photosensitive group unit. The used polyurethane also contains an unsaturated double bond group, a coinitiator structure and a photosensitive group, so that the use of small molecule additives is avoided, the biological safety of the coating on the ureteral stent is improved, the photoinitiation efficiency can be improved, the photocuring energy consumption is reduced, and the curing time is shortened.

Preferably, the molar percentage of the unsaturated double bond group is greater than 3.1%, and the molar percentage of the photosensitive group is less than 20.0%, as determined by $^1$H NMR. Further preferably, in terms of molar percentage, the photocurable polyurethane contains 5.0-15.0% of unsaturated double bond group and 2.8-18.0% of photosensitive group. If the content of the unsaturated double bonds is too low, the degree of curing and crosslinking will be affected, and the firmness and lubricity of the coating are tend to decrease. If the content of the photosensitive group is too high, the crosslinking density after curing will be too high, which will cause a risk that the coating is fragile and is easy to fall off under an external pressure.

The photocurable polyurethane of the present disclosure is obtained at least by the reaction of a polypolyol, an unsaturated polyol containing a tertiary amine group, a polyol containing a benzophenone group, and isocyanate.

The unsaturated polyol containing the tertiary amine group has the following structural formula:

wherein:
X represents —(CH$_2$)$_q$— or —CH(CH$_3$)CH$_2$—, q=1-3;
Y represents O or NH; and
Z represents H or CH$_3$.

The unsaturated polyol has both an unsaturated double bond group and a coinitiator tertiary amine group, the introduction of the tertiary amine group can enhance the energy transfer within the molecules of a polyurethane segment and enhance the initiation efficiency of the photosensitive group, compared with the conventional dihydric alcohols containing amino groups (such as MDEA), the unsaturated polyol in the present disclosure can introduce a longer side chain containing the unsaturated double bond group into the polyurethane, thereby greatly increasing the content of C=C double bonds of the polyurethane and improving the UV curing and crosslinking density. In addition, polar groups in the unsaturated polyol such as ester groups and amide groups can improve the coating power of the polyurethane on polar materials.

In the unsaturated polyol containing the tertiary amine group of the present disclosure, Y is preferably O; further preferably, q=2, Z represents H, that is, the preferred structural formula of the unsaturated polyol containing the tertiary amine group of the present disclosure is:

The polyurethane obtained from the unsaturated polyol containing the tertiary amine group with this structure has better curing and crosslinking properties and can greatly enhance the initiation efficiency of the photosensitive group.

The unsaturated polyol containing the tertiary amine group is prepared by the following method: 1) performing a reaction on (meth) hydroxyalkyl acrylate or hydroxyalkyl (meth) acrylamide and haloacetyl halide to synthesize an intermediate product containing halogen and an unsaturated bond; and 2) performing a reaction on the intermediate product and an amino compound to obtain the unsaturated polyol.

Non-restrictively, in one embodiment of the present disclosure, the unsaturated polyol containing the tertiary amine group is prepared by the following method: performing a reaction on hydroxyethyl acrylate and bromoacetyl bromide to synthesize 2-(2-bromoacetoxy)ethyl acrylate; and performing a reaction on 2-(2-bromoacetoxy)ethyl acrylate and diethanol amine to obtain 2-(N,N-dihydroxyethyl)-2-acetoxyethyl acrylate.

In order to make the polyurethane itself photosensitive, the polyol used for preparing the polyurethane further includes polyols containing photosensitive groups, preferably includes a polyol containing a benzophenone group, such as 4-{3-[bis(2-hydroxyethyl)amino]propoxy} benzophenone, 4-{[bis(2-hydroxyethyl)amino]methyl}benzophenone, 4-{[bis(2-hydroxyethyl)amino]ethyl}benzophenone, 4-[bis(2-hydroxyethyl)amino]benzophenone, 4-[bis(2-hydroxypropyl)amino]benzophenone, and the like, and more preferably 4-{3-[bis(2-hydroxyethyl)amino] propoxy}benzophenone. Reference is made to embodiment 1 in WO2012/062333A for the specific preparation method.

Other common polyols can also be added into the present disclosure. For example, a polyurethane prepolymer can be synthesized by using polypolyol. The molecular weight of the polypolyol is not particularly limited, the number-average molecular weight is preferably not more than 5,000, preferably not more than 2,000, and more preferably not more than 1,000. Examples of the polypolyols include polyester polyols, polyether polyols, polyacetal diols, polysulfide diols, polybutadiene polyols, silicon polyols, polyacrylate polyols, and combinations thereof, and preferably one or a mixture of several of polyether diols, polyester diols, polyacetal diols and polysulfide diols. Suitable polyether polyols include polyethylene glycol, polypropylene glycol and polytetramethylene glycol or block copolymers thereof. Suitable polyester polyols are preferably hydroxylation reaction products of dihydroxy alcohols and polycarboxylic acids, preferably dicarboxylic acids or their corresponding anhydrides, and products obtained by ring-opening polymerization of lactones. The polycarboxylic acids that can be used to form these polyester polyols can be aliphatic, cycloaliphatic, aromatic, and/or heterocyclic polycarboxylic acids and they can be substituted, saturated or unsaturated. Examples of the dicarboxylic acids include succinic acid, glutaric acid, adipic acid, suberic acid, azelaic acid, isophthalic acid, terephthalic acid, phthalic acid, and the like; and the dihydroxy alcohols include ethylene glycol, propanediol, 1,3-propanediol, 1,3-butanediol, 1,4-butanediol, 1,5-pentanediol, 1,6-hexanediol, neopentyl glycol, 1,4-cyclohexanedimethanol, bisphenol A, and the like. The polyester polyols can also adopt polyols such as glycerin, trimethylolethane, trimethylolpropane, and pentaerythritol. In addition, small molecular polyols such as ethylene glycol, diethylene glycol, propanediol, 1,4-butanediol or 1,6-hexanediol can also be used as end-capping agents of polyurethane.

In the present disclosure, aliphatic and aromatic diisocyanates and polyisocyanates are used to prepare the polyurethane prepolymer and the photocurable polyurethane, preferably diisocyanates. However, trifunctional isocyanate or higher functional isocyanate in a small amount, not more than about 20 mol % is also within the scope of the present disclosure. Preferred isocyanates include, but not limited to: aliphatic linear isocyanates, for example including α, ω-alkylene diisocyanates with 5 to 20 carbon atoms, preferably tetramethylene diisocyanate, hexamethylene diisocyanate, trimethyl hexamethylene diisocyanate and the like; cycloaliphatic diisocyanates, such as isophorone diisocyanate and cyclohexane diisocyanate, preferably 1,4-cyclohexane diisocyanate, and fully hydrogenated aromatic diisocyanates, such as hydrogenated tetramethylxylylene diisocyanate, hydrogenated toluene diisocyanate, and hydrogenated methylene diphenylene diisocyanate; and aromatic diisocyanates, such as toluene diisocyanate, especially its 2,4-isomer, methylene diphenylene diisocyanate, tetramethylxylene diisocyanate, and the like. The aromatic diisocyanates can further include polymethylene polyphenylene polyisocyanates with a degree of functionality greater than 2. More than one isocyanate can be used in the present disclosure. One or more of toluene diisocyanate, diphenylmethane diisocyanate, hexamethylene diisocyanate, dicyclohexyl diisocyanate, isophorone diisocyanate and tetramethylxylene diisocyanate are particularly used in the present disclosure preferably.

Non-restrictively, in one embodiment of the present disclosure, the structural formula of the photocurable polyurethane of the present disclosure is as follows:

R represents the residue of polyol;
$R_1$ represents the residue of diisocyanate;
$R_2$ represents —$(CH_2)_p$—, p=1-4;
$R_3$ represents —$(CH_2)_q$—, q=1-3;
$R_4$ represents O or NH; $R_5$ represents H or $CH_3$; and
m, n, e, and f represent the number of repetitive units, and they are all integers not equal to zero; and further, m and n are integers of 1-200, and e and f are integers of 1-100.

The main chain of the polyurethane of this structure has multiple tertiary amine groups, which can partially or completely replace the use of low-molecular-weight tertiary amine additives; the side chain of the polyurethane has the photosensitive group, the aromatic ketone part capture protons of tertiary amine from the carbon atoms of adjacent amino nitrogen, and thus can generate an active group that initiates polymerization or crosslinking; and in addition, the unsaturated double bond group on the side chain can make the polyurethane have a good spontaneous crosslinking function.

Preferably, the photocurable polyurethane of the present disclosure is prepared by the following method:
(1) under the protection of an inert gas, dissolving polyol and diisocyanate in an organic solvent to react to obtain a polyurethane prepolymer-1;
(2) dissolving the unsaturated polyol containing the tertiary amine group, the polyol containing the photosensitive group and a catalyst described in the present disclosure in a solvent, adding the solution into the polyurethane prepolymer-1, and heating to react to obtain a polyurethane prepolymer-2 containing the photosensitive group and the unsaturated group on the side chain; and
(3) adding a small molecule diol into the polyurethane prepolymer-2 for chain extension and end capping to obtain the photocurable polyurethane.

Further preferably, dibutyltin dilaurate is used as the catalyst in step (1), and the reaction is always carried out under the protection of nitrogen, and the polypolyol is preferably one or a mixture of several of polyether diol, polyester diol, polyacetal diol and polysulfide diol; the organic solvent is one or two of butanone, 1,4-dioxane, cyclohexanone, 4-methyl-2-pentanone, acetone, N,N-dimethylformamide and N-methylpyrrolidone, and the reaction of step (1) is preferably carried out at 60-90° C. for 1-4 h. In step (2), the polyol containing the photosensitive group is preferably a polyol containing a benzophenone group, the molar ratio of the unsaturated polyol to the polyol containing the benzophenone group is 2:1 to 1:5, and further preferably 2:1 to 1:2, a polyurethane coating film with good crosslinking degree and peeling strength can be obtained by using the above ratio range; the reaction of step (2) is carried out at 70-90° C. for 2-5 h; and an organometallic compound such as dibutyltin dilaurate is used as the catalyst in step (2). The reaction of step (3) is preferably carried out at 50-70° C. for 1-3 h; and the small molecule diol in step (3) is preferably ethylene glycol or 1,4-butanediol.

The mass concentration of the photocurable polyurethane in the pre-coated coating composition of the present disclosure is 0.1%-50%. If the mass concentration is less than 0.1%, the adhesion ability of the pre-coating on the substrate will decrease, resulting in that the hydrophilic lubricating coating is easy to peel off. If the mass concentration is higher than 50%, the solid content of the coating is high, thus it is difficult to cure completely, and the coating is too thick, which is easy to be unevenly coated, thus affecting the adhesion of subsequent coatings. Further preferably, the range of the mass concentration is 0.5-30%, and more preferably, the range of the mass concentration is 20-30%.

Polymerizable Hydrophilic Polymer

The side chain of the polymerizable hydrophilic polymer of the present disclosure has the unsaturated double bond group. The unsaturated double bonds on the side chain of the hydrophilic polymer can participate in polymerization and cross-linking, and the hydrophilic nature of the polymer can also enhance the connection strength between the pre-coating and the hydrophilic lubricating coating.

The hydrophilic polymer refers to a linear, branched or cross-linked polymer having a high molecular weight and composed of macromolecules, and the polymer has affinity for water or other polar liquid and can provide hydrophilicity for the coating. The hydrophilic polymer can be synthetic or derived from natural products. The hydrophilic polymer can be a homopolymer, a copolymer or a blend. The hydrophilic polymer is mainly polymerized from hydrophilic monomers, refers to a monomer that can dissolve more than 1 g in 100 g of water at 25° C. The hydrophilic monomer includes one or more of unsaturated carboxylic acid or carboxylate, unsaturated carboxylic ester, unsaturated acid hydroxyalkyl ester, unsaturated anhydride, unsaturated amide, unsaturated lactam and epoxyalkane.

Exemplarily, the hydrophilic monomer includes, but not limited to, one or more of (meth)acrylic acid, (meth)acrylamide, vinyl pyrrolidone, (meth)acrylate hydroxyethyl (propyl) ester, vinyl acetate, ethylene oxide, maleic acid, maleic anhydride, fumaric acid, fumaric anhydride and dimethylacrylamide; preferably, the hydrophilic monomer includes one or more of acrylic acid, acrylamide, dimethylacrylamide, hydroxyethyl acrylate and vinyl pyrrolidone; and further preferably, the hydrophilic monomer is acrylamide.

In addition, a small amount of amino-modified unsaturated carboxylate can also be added as a modified monomer to facilitate subsequent graft modification. Examples of the modified monomer include 2-aminoethyl methacrylate hydrochloride, 2-aminopropyl methacrylate hydrochloride and so on.

In one embodiment of the present disclosure, the hydrophilic monomer and the modified monomer are dissolved in water, a free radical initiator is added into the system, oxygen is removed, a reaction is carried out at a certain temperature to obtain the hydrophilic polymer, and then graft modification is performed on the polymer by using (meth) acryloyl chloride or the like to obtain the polymerizable hydrophilic polymer.

Non-restrictively, in one embodiment of the present disclosure, the structural formula of the polymerizable hydrophilic polymer of the present disclosure is as follows:

wherein, $R_6$, $R_7$ and $R_8$ represent H or $CH_3$, g and h represent the number of repetitive units and both are integers not equal to 0, which can be integers of 1-200, and i represents an integer of 1-4.

The mass concentration of the polymerizable hydrophilic polymer in the pre-coated coating composition of the present disclosure is 0.1-30%. If the mass concentration of the polymerizable hydrophilic polymer is less than 0.1%, the crosslinking with the hydrophilic lubricating coating is too weak, and it is difficult to strengthen the firmness between the pre-coating and the hydrophilic lubricating coating. If the mass concentration of the polymerizable hydrophilic polymer is higher than 30%, the adhesion force of the polyurethane is affected, and the firmness of the entire coating is affected. Preferably, the range of the mass concentration is 1-20%.

Solvent

The solvent in the pre-coated coating composition of the present disclosure is a solvent that can dissolve the photocurable polyurethane to form a homogeneous solution, and is preferably one or more of water, low molecular weight alcohol, ethyl acetate, n-hexane, dichloromethane, trichloromethane, N,N-dimethylformamide, N,N-dimethylacetamide, dimethyl sulfoxide, acetone, ether, toluene, benzene, xylene, cyclohexane and phenol. Further preferably, the solvent of the present disclosure is water and isopropanol. More preferably, the volume ratio of water to isopropanol is 1:10 to 10:1.

The pre-coated coating composition of the present disclosure can be obtained by dissolving the photocurable polyurethane and the polymerizable hydrophilic polymer of the present disclosure in a suitable solvent. The solvent can then be evaporated or remain in the coating and act as a swelling medium that provides the desired gel.

<Hydrophilic Lubricating Coating Composition>

In the present disclosure, the hydrophilic lubricating coating is formed by a hydrophilic lubricating coating composition, the hydrophilic lubricating coating composition contains a photocurable polymer, and the photocurable polymer is copolymerized by a water-soluble polymerizable photosensitive monomer and a hydrophilic monomer.

Water-Soluble Polymerizable Photosensitive Monomer

The water-soluble polymerizable photosensitive monomer of the present disclosure contains: 1) a unit containing a photosensitive structure; 2) a unit containing a quaternary ammonium salt structure; and 3) a unit containing an unsaturated bond structure; and the unit containing a photosensitive structure is connected to the unit containing a quaternary ammonium salt structure at least through —C(=O)—, and the unit containing an unsaturated bond structure is connected to the unit containing a photosensitive structure through the unit containing a quaternary ammonium salt structure.

In addition to the photoinitiating unit (that is, the unit containing the photosensitive structure), the molecular structure of the water-soluble polymerizable photosensitive monomer further contains quaternary ammonium salt ions and double bonds, so that the photosensitive monomer has both water solubility and polymerizability, it not only has good compatibility with water-base resin, but also is polymerized to the macromolecular chain of the resin, which can effectively overcome the defect of easy migration of small molecules to the surface of the product.

In one embodiment of the present disclosure, the unit containing the photosensitive structure is derived from a cleavage-type hydroxyphenone photoinitiator, and is preferably derived from a substituted or unsubstituted α-hydroxyalkylphenone photoinitiator. More specifically, the α-hydroxyalkylphenone photoinitiator has the following structure: $R^3$-Ph-C(=O)—C($R^1$)($R^2$)OH (II).

Wherein: $R^1$ and $R^2$ are independently selected from hydrogen, $C_1$-$C_6$ alkyls, phenyl, $C_1$-$C_6$ hydroxyalkyls or $R^1$ and $R^2$ together with carbon atoms to which they are connected form a cyclohexyl ring; $R^3$ is selected from hydrogen, $C_1$-$C_6$ alkyls, $C_1$-$C_6$ alkoxies, $C_1$-$C_6$ hydroxyalkyls, and —OCH$_2$CH$_2$—OR$_4$; and $R_4$ is selected from hydrogen, and $C_1$-$C_6$ alkyls.

Specifically, the α-hydroxyalkylphenone photoinitiator can be selected from 2-hydroxyl-2-methyl-1-phenyl-1-propanone, 1-hydroxyl-cyclohexyl-phenyl-methanone, 2-hydroxyl-4'-(2-hydroxyethoxy)-2-methylpropiophenone, (4-isopropylphenyl)-1-propanone, 2-hydroxyl-2-methyl-1-2-hydroxyl-2-methyl-1-(4-tert-butylphenyl)-1-acetone; the α-hydroxyalkylphenone photoinitiator is preferably selected from any one of 2-hydroxyl-2-methyl-1-phenyl-1-propanone, 1-hydroxyl-cyclohexyl-phenyl-methanone, 2-hydroxyl-4'-(2-hydroxyethoxy)-2-methylpropiophenone, 2-hydroxyl-2-methyl-1-(4-isopropylphenyl)-1-propanone and 2-hydroxyl-2-methyl-1-(4-tert-butylphenyl)-1-acetone; and from the viewpoint of improving the initiation activity and the yellowing resistance, the α-hydroxyalkylphenone photoinitiator is more preferably selected as 2-hydroxyl-4'-(2-hydroxyethoxy)-2-methylpropiophenone.

The α-hydroxyalkylphenone photoinitiator contains a carbonyl and an α-hydroxyl double active functional group, so that this type of photoinitiators has active chemical properties and has strong derivatization ability. This type of photoinitiators is not only suitable for general photopolymerization systems, but also is more applicable to emulsion or latex photopolymerization systems and water-soluble photopolymerization systems. This type of photoinitiators belongs to a cleavage-type free radical photoinitiator, but compared with other common cleavage-type photoinitiators such as benzoin ether, it has good yellowing resistance and thermal stability, and compared with hydrogen abstraction-type free radical photoinitiators such as benzophenone (BP), it has high photoinitiation activity and good yellowing resistance. The inventor of the present disclosure finds that when the photosensitive structure unit of the present disclosure is derived from the α-hydroxyalkylphenone photoinitiator, better photoinitiation efficiency, yellowing resistance and thermal stability can be obtained compared with other types of photoinitiators, moreover, the volatility can also be reduced, wherein the effect of 2-hydroxyl-4'-(2-hydroxyethoxy)-2-methylpropiophenone is particularly effective. The inventor speculates that because the benzene ring in its structure is directly connected to an oxygen atom, the two unique pairs of electrons on the oxygen atom can be conjugated with the benzene ring, so that the electron density of the benzene ring is increased, as a result, the probability of electrons being excited to transition is increased, and the benzene ring acts with other groups (such as nitrogen-containing groups, and unsaturated double bonds) to greatly improve the photoinitiation activity; and the reduction of volatility is related to the long side chain of the benzene ring.

The presence of quaternary ammonium salt can greatly improve the water solubility, while also having certain antibacterial property. The unit containing the quaternary ammonium salt structure contains a quaternary ammonium salt group, and in addition, can also contain several alkylene groups.

The unit containing the unsaturated bond structure can be a polymerizable group containing double bonds. Such a reactive group can enable the photosensitive unit to be incorporated into the main chain of the polymer by means of free radical polymerization in the form of a repetitive unit. The unit containing the unsaturated bond structure can be selected from units having (meth)acrylate groups. The presence of the polymerizable group can overcome the problems of toxicity and high migration rate of conventional small molecule photoinitiators, and promote the anchoring of the photoinitiators in a polymer network, can also improve the material properties through copolymerization with other monomers, and meanwhile inhibit undesirable volatilization caused by residual small molecule photoinitiators.

In a preferred solution of the present disclosure, the unit containing the photosensitive structure is directly connected to the quaternary ammonium salt structure through a carbonyl (—C(=O)—), and the unit containing the unsaturated bond structure is directly connected to the unit containing the photosensitive structure through the unit containing the quaternary ammonium salt structure. This connection mode provides the greatest opportunity for the interaction between the various structural units, is conducive to energy transfer, can generate more free radical active species more quickly, and improves the initiation efficiency.

In a preferred embodiment of the present disclosure, the water-soluble polymerizable photosensitive monomer has a structure shown by general formula (I):

wherein: $R_1$=CH$_3$ or H; $R_2$ and $R_3$ are independently selected from linear alkyls having 1 to 20 C atoms or branched alkyls having 3 to 20 C atoms, respectively;

X represents halogen; n=1-10; m=1-4; f=1-3; preferably, $R_2$ and $R_3$ are the same, X represents bromine, n=1, m=1, and f=1; and more preferably, $R_2$ and $R_3$ are both methyl or ethyl, X represents bromine, n=1, m=1, and f=1. The choice of the groups and molecular chain length in the general formula is mainly based on the requirements of viscosity, initiation rate and migration of the comprehensive product.

Further preferably, the suitable water-soluble polymerizable photosensitive monomer according to the present disclosure includes one or more compounds of the following structure:

The water-soluble polymerizable photosensitive monomer of the present disclosure is obtained by performing acyl halogenation treatment on a molecular tail end of a compound containing a photosensitive structure, and then performing a reaction with (meth) acrylate containing a tertiary amino group.

Exemplarily, the reaction process of the water-soluble polymerizable photosensitive monomer is as follows:

wherein, $R_1$ and $R_2$ have the same definition as the general formula (I).

Preferably, the molar concentration of the water-soluble polymerizable photosensitive monomer in the photocurable polymer is 0.08-12%, preferably 0.5-8%, further preferably 3-7.5%, more preferably 3-5%, and most preferably 4%. By using the specific molar concentration, the lowest friction force (about 0.125 N) can be obtained, and the friction force hardly increases with the increase of the number of cycles, and the friction force does not increase significantly after more than 30 cycles.

Hydrophilic Monomer

The hydrophilic monomer refers to a monomer that can dissolve more than 1 g in 100 g of water at 25° C. The water-soluble polymerizable photosensitive monomer and the hydrophilic monomer can be copolymerized to obtain a hydrophilic photocurable polymer. The hydrophilic monomer is mainly used for providing hydrophilicity for the polymer.

The hydrophilic monomer includes one or more of unsaturated carboxylic acid or carboxylate, unsaturated carboxylic ester, unsaturated acid hydroxyalkyl ester, unsaturated anhydride, unsaturated amide, unsaturated lactam and epoxyalkane.

Exemplarily, the hydrophilic monomer includes, but not limited to, one or more of (meth)acrylic acid, (meth)acrylamide, vinyl pyrrolidone, (meth)acrylate hydroxyethyl (propyl) ester, vinyl acetate, ethylene oxide, maleic acid, maleic anhydride, fumaric acid, fumaric anhydride and dimethylacrylamide; and preferably, the hydrophilic monomer includes one or more of acrylic acid, acrylamide, dimethylacrylamide, hydroxyethyl acrylate and vinyl pyrrolidone.

In the above hydrophilic monomer, the structure of vinyl pyrrolidone (NVP) gives it and its polymers special properties: the vinyl pyrrolidone is easy to polymerize, and its polymer has excellent hydrophilicity, complexing ability and physiological compatibility, good chemical stability, and no irritation to the skin; and the vinyl pyrrolidone has a strong solubilizing effect, can increase the water solubility of some pharmacologically active substances that are basically insoluble in water, and thus is suitable for medical use. Therefore, in the present disclosure, it is more preferable that the hydrophilic monomer is vinyl pyrrolidone. The present disclosure further surprisingly finds that when vinyl pyrrolidone is used as the hydrophilic monomer, the resulting hydrophilic coating has a better lubricating effect, which is prominently reflected in the low friction force, and as the number of cycles increases, the friction force almost has no change.

Polymerization

The photocurable polymer in the present disclosure is prepared by a free radical polymerization method, including, but not limited to, ordinary free radical polymerization and activity controllable free radical polymerization. Preferably, the photocurable hydrophilic polymer is prepared by an ordinary free radical polymerization method. The photocurable polymer is prepared in a certain medium, including, but not limited to, solution polymerization, emulsion polymerization, reverse emulsion polymerization, suspension polymerization and bulk polymerization. From the perspective of easy operation, preferably, the photocurable hydrophilic polymer is prepared by solution polymerization, and from the perspective of environmental protection, more preferably, the photocurable polymer is copolymerized in an aqueous solution. In one embodiment of the present disclosure, the water-soluble polymerizable photosensitive monomer and the hydrophilic monomer are dissolved in water, a free radical initiator is added into the system, oxygen is removed, and a reaction is carried out at a specific temperature to obtain the photocurable polymer.

The concentration of the monomer contained in the aqueous solution is preferably between 10% and 50% by weight of the solution, more preferably between 10% and 30%, and still more preferably between 12% and 20%.

In the polymerization reaction, the free radical initiator refers to a substance that can generate free radicals when activation energy is applied, and includes a thermal activation initiator, such as organic peroxides, organic hydrogen peroxide and azoic compounds. Representative examples of these initiators include, but not limited to, benzoyl peroxide, tert-butyl perbenzoate, diisopropyl peroxydicarbonate, cumene hydroperoxide, azobisisobutyronitrile, and the like. In a preferred embodiment of the present disclosure, the free radical initiator is azobisisobutyronitrile. The thermal initiator is usually used in a dosage of 0.01-5% by mass of the monomer, and preferably 0.02-0.05%.

In order to reduce the mobility, the photocurable polymer preferably has a number-average molecular weight of at least 50,000, a photocurable polymer having a relatively high molecular weight is preferred, but for the ease of application of the coating, the molecular weight is preferably 1 million or less. In order to obtain a hydrophilic coating that has good lubricity after multiple cycles, preferably, the number-average molecular weight of the photocurable polymer is preferably 50,000-700,000, further preferably 100,000-500,000, and most preferably 300,000-400,000.

In a preferred embodiment of the present disclosure, the hydrophilic lubricating coating composition includes the photocurable polymer, a solvent and optional ingredients.

The mass concentration of the photocurable polymer in the hydrophilic lubricating coating composition is 0.5-10%, preferably, the mass concentration is 2.5-7.5%, and more preferably 5%.

The mass concentration of the solvent in the hydrophilic lubricating coating composition is 90-99.5%, preferably, the mass concentration is 92.5-97.5%, and more preferably 95%.

Solvent

Any solvent that is allowed to be coated with the hydrophilic coating composition on the surface meets the requirements of the hydrophilic lubricating coating composition. Preferably, the solvent is one or a mixed solvent that can dissolve the photocurable polymer to form a homogeneous solution. The example of the solvent includes one or more of water, low molecular weight alcohols (methanol, ethanol, isopropanol, butanol, pentanol, ethylene glycol, propylene glycol, glycerol or the like), ethyl acetate, n-hexane, methylene chloride, trichloromethane, N,N-dimethylformamide, N,N-dimethylacetamide, dimethyl sulfoxide, acetone, ether, toluene, benzene, xylene, cyclohexane and phenol. In order to achieve dissolution and uniform mixing, low cost and non-pollution, the solvent is preferably a mixture of water and isopropanol, and preferably, the volume ratio of water to isopropanol is 1:10 to 10:1. In order to achieve dissolution and uniform mixing, the volume ratio of water to isopropanol is more preferably 1:5 to 5:1, and is most preferably 2:3 to 3:2.

Optional Ingredients

Lubricating additives such as surfactant, wax, lubricant, soap and detergent can also be added into the hydrophilic lubricating coating composition as needed. These lubricating additives will not increase the osmolarity of the coating too much, but can increase the lubricity when wetting and reduce the adhesion. Their low solubility in water helps to keep them in the coating. Other additives can include supporting polymers, polyelectrolytes, wetting agents, leveling agents, defoamers, film forming aids, thickeners, pigments, antibacterial agents, colorants, surfactants, and the like. Preferably, in a specific embodiment of the present disclosure, the hydrophilic lubricating coating composition can obtain good lubricity and firmness without adding additional optional ingredients except for the photocurable polymer and the solvent.

<Preparation of the Ureteral Stent>

The present disclosure further provides a preparation method of the ureteral stent, wherein at least one pre-coating is formed on the surface of the ureteral stent, then at least one hydrophilic lubricating coating is formed on the pre-coating, and preferably, the pre-coating and the hydrophilic lubricating coating are formed by photocuring, thermal curing, chemical reaction, physical adsorption, crystallization or freezing.

Formation of the Pre-Coating

The pre-coating is formed, for example, in the following manner: coating the pre-coated coating composition of the present disclosure on the surface of the ureter, for example by dip coating, and then exposing the pre-coated coating composition to electromagnetic radiation, preferably ultraviolet radiation, so as to activate the photosensitive group unit in the photocurable polyurethane to cure the pre-coated coating composition. The ultraviolet light intensity during curing is 5-25 mW/cm$^2$, and the curing time of the pre-coated coating composition is 2-10 min.

As a non-restrictive example, the pre-coating can be formed in the following manner.

An appropriate amount of photocurable polyurethane is weighed, and preferably its mass concentration in the pre-coated coating composition is 20%-30%. The polymerizable hydrophilic polymer whose mass concentration in the pre-coated coating composition is preferably 1-20% is dissolved in a mixed solvent of water and isopropanol. The ureteral stent is immersed in a charging barrel holding the pre-coated coating composition that contains the photocurable polyurethane and the polymerizable hydrophilic polymer of the present disclosure, and is standed still for 0.5-2 min, the catheter is lift at a speed of 0.5-1 cm/s, the catheter with masking liquid is irradiated with an ultraviolet lamp with ultraviolet light intensity of 5-25 mW/cm² for 2-5 min to perform curing treatment, the rotation speed of the catheter is 3-6 rpm, and the cured sample is placed in the air to dry to obtain a catheter with a pre-coating. The thickness of the pre-coating on the ureter is preferably within the range of 1-20 μm.

Formation of the Hydrophilic Lubricating Coating

Preferably, the hydrophilic lubricating coating can be coated on the surface of the pre-coating when the pre-coating is completely dry or semi-dry.

As a non-restrictive example, the hydrophilic lubricating coating can be formed in the following manner.

An appropriate amount of photocurable polymer (based on the total amount of the hydrophilic lubricating coating composition, the mass concentration is preferably 0.5-10%) is weighed and is dissolved in one or more solvents of water, low molecular weight alcohols (methanol, ethanol, isopropanol, butanol, pentanol, ethylene glycol, propylene glycol, glycerol or the like), ethyl acetate, n-hexane, methylene chloride, trichloromethane, N,N-dimethylformamide, N,N-dimethylacetamide, dimethyl sulfoxide, acetone, ether, toluene, benzene, xylene, cyclohexane and phenol.

Lubricating additives such as surfactant, wax, lubricant, soap and detergent can also be added into the hydrophilic lubricating coating composition as needed. These lubricating additives will not increase the osmolarity of the coating too much, but can increase the lubricity when wetting and reduce the adhesion. Their low solubility in water helps to keep them in the coating. Other additives can include supporting polymers, polyelectrolytes, wetting agents, leveling agents, defoamers, film forming aids, thickeners, pigments, antibacterial agents, colorants, surfactants, and the like. The ureteral stent with the pre-coating is immersed into the charging barrel containing a masking liquid composition and is standed still for 2-7 min, the catheter is lift at a speed of 0.5-1 cm/s, the coating method can be one or more of brushing, dip coating, spray coating, flow coating and knife coating, the masking liquid composition is coated on the pre-coating of the ureteral stent, the ureteral stent with the masking liquid is irradiated with an ultraviolet lamp with ultraviolet light intensity of 5-25 mW/cm² for 3-5 min to perform curing treatment, and the cured sample is placed in the air to dry to obtain the ureteral stent with the hydrophilic lubricating coating. The thickness of the hydrophilic lubricating coating on the ureteral stent is preferably within the range of 1-20 μm.

The thickness of the pre-coating and the hydrophilic lubricating coating can be controlled by the following methods: changing the soaking time, changing the lifting rate, or changing the viscosity of the coating composition and the number of coating steps. Generally, the thickness of the pre-coating on the ureteral stent is within the range of 0.1-100 μm, preferably within the range of 0.5-50 μm, and more preferably within the range of 1-20 μm. The thickness of the hydrophilic lubricating coating on the ureteral stent is within the range of 0.1-200 μm, preferably within the range of 0.5-100 μm, and more preferably within the range of 1-20 μm.

Materials suitable for producing the ureteral stent include polymers, such as polyurethane, copolymers (such as polyether block amide known as PEBAX), polyamide, silicone, polyolefin, polyamide, polyvinyl chloride (PVC), thermoplastic polyurethane, aromatic polyether, aromatic polyester and aliphatic polyester having a Shore hardness generally between 25 and 95, thermoplastic elastomer-based compounds, vulcanized thermoplastic elastomers, thermoplastic polyurethane-based mixtures and co-blends, ethylene vinyl acetate (EVA), etc.

EMBODIMENTS

The following embodiments are given to illustrate the present disclosure. Those skilled in the art can understand that the examples are only exemplary descriptions, not exhaustive descriptions.

Testing Method

The content of the unsaturated double bonds and the content of the photosensitive group are measured by $^1$H NMR spectroscopy.

Friction Force Test:

The ureteral stent is clamped by double clamping pieces, the clamping pieces are placed in deionized water, a certain pressure is applied through the clamping pieces, and the force required to lift the ureteral stent is tested to obtain a friction force test result. The used clamping force is 300 g, the lifting speed is 10 mm/s, and the test cycle is 30 times.

Embodiment 1

Figure 1:
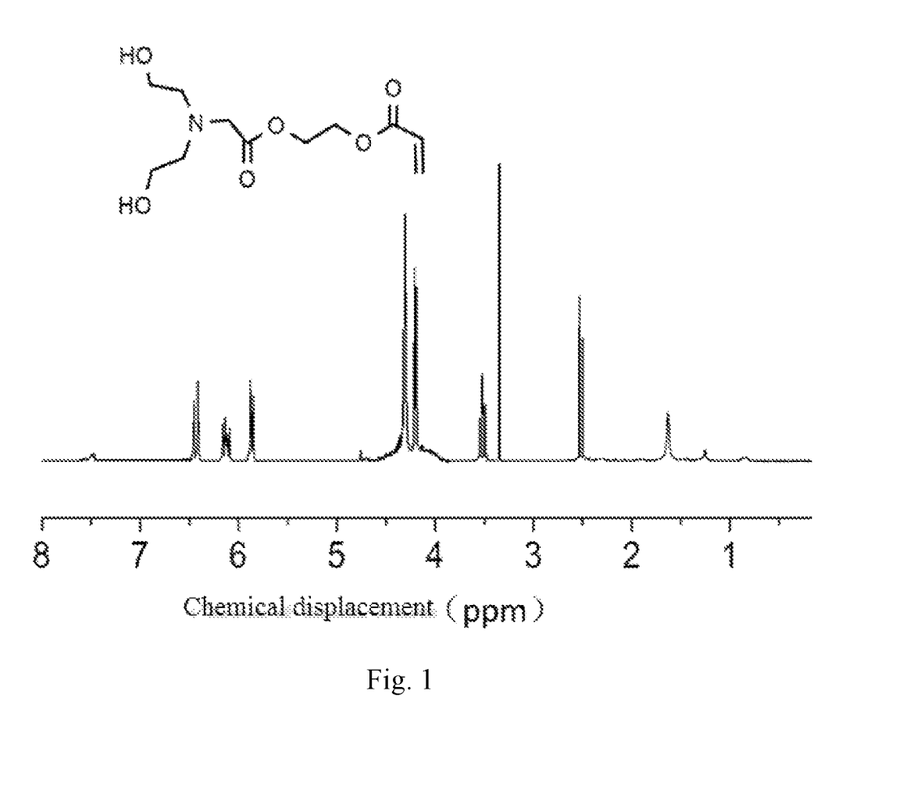
FIG. 1 is a magnetic resonance imaging hydrogen spectrum ($^1$H NMR) spectrogram of 2-(N,N-dihydroxyethyl)-2-acetoxyethyl acrylate prepared in an embodiment.

Step 1: Synthesis of the Photocurable Polyurethane
  (1) Preparation of the unsaturated polyol containing the tertiary amine group:
    Dissolving hydroxyethyl acrylate (11.5 mL, 0.1 mol) in dichloromethane, dripping bromoacetyl bromide (9.6 mL, 0.11 mol) into the solution at a low temperature (0° C.), the molar ratio of bromoacetyl bromide to hydroxyethyl acrylate is 1.1:1, reacting for 0.5 h under the action of sodium hydroxide (4 g, 0.1 mol), heating up to 30° C., continuing to react for 16 h, and performing purification and drying to obtain 2-(2-bromoacetoxy)) ethyl acrylate (16.5 g, the yield is 70%); and afterwards, dissolving 2-(2-bromoacetoxy)) ethyl acrylate (11.8 g, 0.05 mol) and diethanolamine (6.3 g, 0.06 mol) in dioxane, reacting for 5 h at 60° C. under the catalysis of triethylamine (6.1 g, 0.06 mol), and performing separation, purification and drying to obtain 2-(N,N-dihydroxyethyl)-2-acetoxyethyl acrylate (10.2 g, the yield is 78%). The magnetic resonance imaging spectrum of the product is shown in FIG. 1.
    $^1$H NMR (δ/ppm): 2.51 (m, 4H, CH$_2$), 3.35 (s, 2H, CH$_2$), 3.52 (m, 4H, CH$_2$), 4.28 (m, 2H, CH$_2$), 4.38 (m, 2H, CH$_2$), 5.83 (m, H, CH=CH$_2$), 6.12 (m, H, CH=CH$_2$), 6.45 (m, H, CH=CH$_2$). The assignment and integration area of each characteristic peak are consistent with the structure of the target product.
  (2) Under the protection of nitrogen, adding 3.5 g of toluene diisocyanate into a round bottom flask equipped with a thermometer, a condenser pipe and a stirrer, placing the round bottom flask in an oil bath at 75° C., dripping 10 g of polypropylene glycol into a four-necked reaction flask by using a constant pressure funnel, carrying out a heat preservation reaction for 2.5 h, and adjusting the viscosity of the reaction liquid with acetone to obtain the polyurethane prepolymer-1.

(3) Dissolving 2.6 g of the aforementioned unsaturated polyol and 1.7 g of 4-{3-[bis(2-hydroxyethyl)amino]propoxy}benzophenone (the molar ratio of the two is 2/1) in DMF, adding the solution into the polyurethane prepolymer-1, adding 0.1 g of dibutyltin dilaurate as the catalyst, and reacting at 65° C. for 3 h to obtain the polyurethane prepolymer-2 containing the photosensitive group and the unsaturated double bond group on the side chain.

(4) Cooling to 50° C., adding 1.8 g of 1,4-butanediol into the polyurethane prepolymer-2 by using a dropping funnel, reacting at 60° C. for 2 h, and carrying out chain extension and end capping to obtain the photocurable polyurethane.

Figure 2:
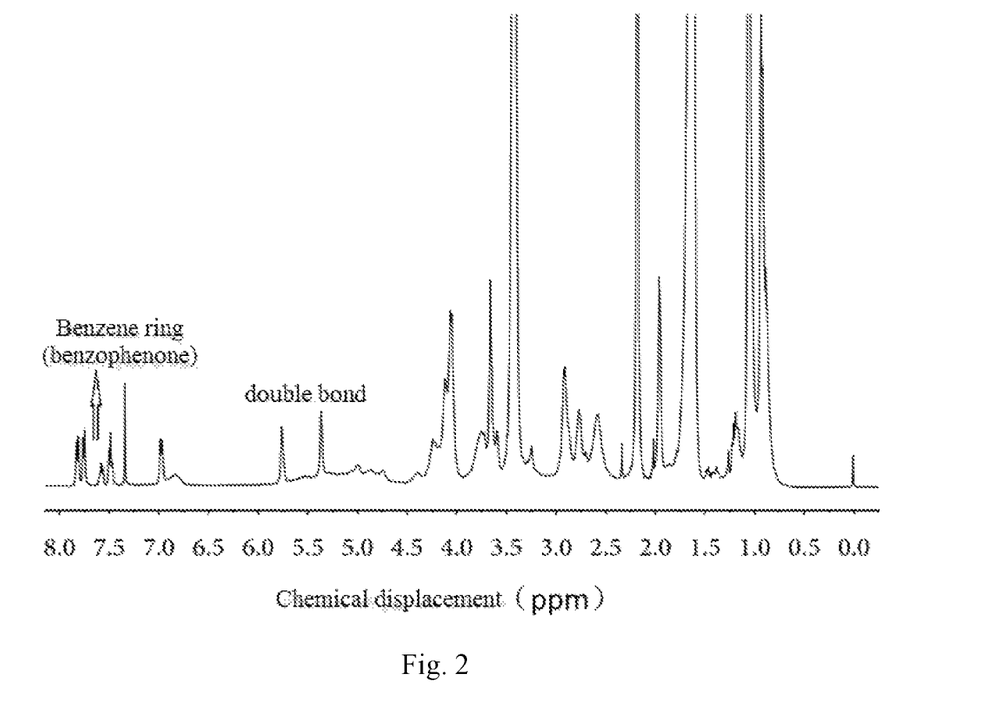
FIG. 2 is a magnetic resonance imaging hydrogen spectrum ($^1$H NMR) spectrogram of photocurable polyurethane prepared in an embodiment.

The nuclear magnetic resonance imaging spectrum of the obtained photocurable polyurethane is shown in FIG. 2. It can be seen from FIG. 2 that 1.2-4.6 ppm corresponds to the characteristic peak of the main chain structure of the polyurethane, the characteristic peak at 7.43-7.85 ppm proves the presence of benzene rings in the polyurethane, and the peak at 5.72-5.79 ppm proves the existence of double bonds in the polyurethane, and it is measured that the molar percentage of the unsaturated double bonds is 8.4%, and the molar percentage of the benzophenone group is 10.0%.

Step 2:

Weighing 10 g of acrylamide, 0.365 g of 2-aminopropyl methacrylate hydrochloride, and 0.115 g of azobisisobutyronitrile, dissolving the same in 20 mL of DMF, and reacting at 60° C. for 6 h. After the reaction, precipitating and drying by using ethanol to obtain a hydrophilic polymer A.

Weighing 5 g of hydrophilic polymer A and 0.144 g of methacryloyl chloride, dissolving the same in 10 mL of DMF, reacting for 20 h at room temperature, and after the reaction is completed, precipitating and drying by using ethanol to obtain a polymerizable hydrophilic polymer B.

Step 3:

Weighing the prepared photocurable polyurethane and the polymerizable hydrophilic polymer B, and preparing the pre-coated coating composition in which the mass fraction of the photocurable polyurethane is 30%, the mass fraction of the polymerizable hydrophilic polymer B is 10%, and the mixed solvent accounted for 60%, wherein the mixed solvent is composed of isopropanol and water, and the volume ratio of the ingredients is 1:1.

Wiping the surface of the ureteral stent made of polyurethane with a dust-free cloth soaked in 75% ethanol and drying the same. Immersing the ureteral stent in a material tube containing the above-mentioned pre-coated coating composition, standing still for 1min, lifting the ureteral stent at a speed of 0.5 cm/s, irradiating the ureteral stent with the masking liquid with an ultraviolet lamp for 2 min to perform curing treatment, wherein the ultraviolet light intensity is 10 mW/cm$^2$, the rotation speed of the ureteral stent is 4 rpm, and the ureteral stent with the pre-coating is obtained after the curing is completed.

Step 4:

(1) Synthesis of the Water-Soluble Polymerizable Photosensitive Monomer

Dissolving 22.4 g (100 mmol) of 2-hydroxyl-4'-(2-hydroxyethoxy)-2-methylpropiophenone and 10.6 g (105 mmol) of triethylamine in 100 mL of dichloromethane, putting the solution in a 250 mL flask, and placing the flask in an ice-water bath to fully dissolve the ingredients. Slowly dripping 9.1 mL of dichloromethane solution of bromoacetyl bromide (21.1 g, 105 mmol) into the flask within 1 h. After reacting for 0.5 h under an ice bath condition, heating up to room temperature to continue the reaction for 10 h. After the reaction is completed, cooling to room temperature and dissolving the crude product in dichloromethane, washing with saturated saline solution, hydrochloric acid (IM) and saturated sodium bicarbonate successively twice, drying over overnight via anhydrous magnesium sulfate, filtering and spin drying the solvent, using ethyl acetate and n-hexane as eluents, and obtaining 28.8 g of 2-hydroxyl-4'-(2-hydroxyethoxy bromoacetate)-2-methylpropiophenone after purification by column chromatography, wherein the product is a white solid, and the yield is 84%.

Dissolving 6.9 g (20 mmol) of 2-hydroxyl-4'-(2-hydroxyethoxy bromoacetate)-2-methylpropiophenone and 0.05 g of hydroquinone in 50 mL of acetonitrile, placing the solution in a 250 mL flask to fully dissolve the ingredients. Slowly dripping 50 mL of acetonitrile solution of dimethylaminoethyl methacrylate (3.2 g, 20 mmol) into the flask, and heating up to 60° C. to react for 12 h. After the reaction is completed, spin drying the solvent, precipitating the product with anhydrous ether, and obtaining 10 g of water-soluble polymerizable photosensitive monomer after purification by column chromatography. As shown in the structural formula (I), the water-soluble polymerizable photosensitive monomer is pale yellow viscous liquid with a yield of 100%. The results of magnetic resonance imaging hydrogen spectrum (1H NMR) are as follows:

1.35 ppm (m, 6H, CH$_3$—C—OH), 1.98 ppm (m, 3H, CH$_3$—C=), 3.30 ppm (m, 6H, CH$_3$—N), 3.48 ppm (m, 2H, —CH$_2$—N), 4.2 ppm (s, 2H, O=C—CH$_2$—), 4.44-4.6 ppm (m, 6H, —CH$_2$—O), 6.4-6.5 ppm (m, 2H, —CH$_2$), 7.01-7.94 ppm (m, 4H, benzene ring)

Structural formula I (2) Synthesis of the Photocurable Polymer

Weighing 106.7 g (0.96 mol) of vinyl pyrrolidone, 16.9 g (0.04 mol) of the above-mentioned water-soluble polymerizable photosensitive monomer and 0.0618 g (0.05% by mass fraction of total monomer) azodiisobutyronitrile and adding the same into a 1 L round-bottom flask, adding 700 mL of deionized water, and performing mechanical stirring to dissolve the ingredients. Filling N2 to deoxidize the solution for 30 min, and placing the reaction flask in an oil bath to heat at 65° C. so as to start the reaction. After 6 hours of reaction, taking off and cooling the reaction solution to room temperature, precipitating the solution with 95% ethanol, and drying the precipitate in an oven at 35° C. in the dark for 36 h. The number-average molecular weight Mn of the obtained polymer measured by GPC is 396,000, and the molecular weight distribution PDI is 1.91.

Step 5:

Weighing 5 g of photocurable polymer (Mn=396,000, the molar fraction of the water-soluble polymerizable photosensitive monomer is 4%), and adding the same into 95 g of mixed solvent of deionized water/isopropanol (the volume ratio is 1:1), and stirring in the dark for 18 h to dissolve the photocurable polymer. The resulting solution is a colorless and clear solution.

Immersing the ureteral stent with the pre-coating in the charging barrel containing the above-mentioned masking liquid composition, standing still for 1 min, lifting the ureteral stent at a speed of 0.5 cm/s, irradiating the ureteral stent with the masking liquid with an ultraviolet lamp for 5 min to perform curing treatment, wherein the ultraviolet light intensity is 10 mW/cm$^2$, and the rotation speed of the ureteral stent is 4 rpm. The cured sample is placed in the air for drying. The thickness of the hydrophilic lubricating coating prepared by the process is within 2-10 μm.

Step 6:

The obtained coating of the ureteral stent is visually observed without obvious unevenness, and is placed on a clamping piece type friction force tester to test the lubricating performance. The test results are shown in Table 1.

TABLE 1

|  | Initial friction force (N) | Friction force of the 30$^{th}$ cycle (N) | Friction force of the 30$^{th}$ cycle/initial friction force |
| --- | --- | --- | --- |
| Ureteral stent | 0.240 | 4.250 | 17.71 |
| Ureteral stent + coating | 0.125 | 0.138 | 1.15 |

It can be seen that, in the present disclosure, a pre-coating is formed on the surface of the ureteral stent with a more complicated shape, and then the hydrophilic lubricating coating is formed on the ureteral stent with the pre-coating, so that the friction force (the friction force of the 30th cycle is small, and the friction force of the 30th cycle/initial friction force is kept within 2 times) of the ureteral stent can be greatly reduced, the lubricating performance is greatly improved, and the formed coating is stable and firm.

Embodiments 2-5

The hydrophilic monomer vinyl pyrrolidone in step 4 of embodiment 1 is replaced with acrylic acid, acrylamide, dimethacrylamide and hydroxyethyl acrylate to prepare a series of photocurable polymers with similar molecular weights (respectively embodiments 2-5). The other steps are the same as those in embodiment 1. The lubricating performance of the prepared ureteral stent is evaluated, and the results are shown in Table 2.

TABLE 2

The influence of the category of the hydrophilic monomer on the performance of the coating of the polyurethane ureteral stent

| Hydrophilic monomer | Initial friction force (N) | Friction force of the 30$^{th}$ cycle (N) | Friction force of the 30$^{th}$ cycle/initial friction force |
| --- | --- | --- | --- |
| Acrylic acid | 0.250 | 0.274 | 1.10 |
| Acrylamide | 0.175 | 0.196 | 1.12 |
| Dimethacrylamide | 0.225 | 0.246 | 1.09 |
| Hydroxyethyl acrylate | 0.250 | 0.286 | 1.14 |
| Vinyl pyrrolidone | 0.125 | 0.138 | 1.15 |

It can be seen from Table 2 that by this method, a stable and firm hydrophilic lubricating coating can be constructed on the surface of the ureteral stent, and for different hydrophilic monomers, vinyl pyrrolidone has the best lubricating performance.

What is claimed is:

1. A ureteral stent, comprising at least one pre-coating formed on its surface and at least one hydrophilic lubricating coating formed on the pre-coating, wherein the pre-coating is formed by a pre-coated coating composition, the pre-coated coating composition comprises photocurable polyurethane, a polymerizable hydrophilic polymer and a solvent, the main chain of the photocurable polyurethane contains a tertiary amine group, the side chain thereof has an unsaturated double bond group and a photosensitive group unit, and the side chain of the polymerizable hydrophilic polymer has an unsaturated double bond group; and the hydrophilic lubricating coating is formed by a hydrophilic lubricating coating composition, the hydrophilic lubricating coating composition comprises a photocurable polymer, the photocurable polymer is copolymerized by a water-soluble polymerizable photosensitive monomer and a hydrophilic monomer, the water-soluble polymerizable photosensitive monomer contains: 1) a unit containing a photosensitive structure; 2) a unit containing a quaternary ammonium salt structure; and 3) a unit containing an unsaturated bond structure; and the unit containing a photosensitive structure connected to the unit containing a quaternary ammonium salt structure at least through —C(=O)—, and the unit containing an unsaturated bond structure connected to the unit containing a photosensitive structure through the unit containing a quaternary ammonium salt structure.

2. The ureteral stent according to claim 1, wherein
the mass concentration of the photocurable polyurethane in the pre-coated coating composition is 0.1-50%, preferably, the range of the mass concentration is 0.5-30%, and more preferably, the range of the mass concentration is 20-30%; and the mass concentration of the polymerizable hydrophilic polymer in the pre-coated coating composition is 0.1-30%, and preferably, the range of the mass concentration is 1-20%; and
the mass concentration of the photocurable polymer in the hydrophilic lubricating coating composition is 0.5-10%, preferably, the mass concentration is 2.5-7.5%, and more preferably 5%.

3. The ureteral stent according to claim 1, wherein the solvent is a solvent that can dissolve the photocurable polyurethane to form a homogeneous solution, and is preferably one or more of water, low molecular weight alcohol, ethyl acetate, n-hexane, dichloromethane, trichloromethane, N,N-dimethylformamide, N,N-dimethylacetamide, dimethyl sulfoxide, acetone, ether, toluene, benzene, xylene, cyclohexane and phenol.

4. The ureteral stent according to claim 1, wherein
the photocurable polyurethane is obtained at least by the reaction of a polypolyol, an unsaturated polyol containing a tertiary amine group, a polyol containing a benzophenone group, and isocyanate.

5. The ureteral stent according to claim 1, wherein
the structural formula of the photocurable polyurethane is as follows:

R represents the residue of polyol;
R$_1$ represents the residue of diisocyanate;
R$_2$ represents —(CH$_2$)$_p$—, p=1-4;
R$_3$ represents —(CH$_2$)$_q$—, q=1-3;
R$_4$ represents O or NH; R$_5$ represents H or CH$_3$; and
m, n, e, and f represent the number of repetitive units, and they are all integers not equal to zero.

6. The ureteral stent according to claim 1, wherein the structural formula of the polymerizable hydrophilic polymer is as follows:

wherein, R$_6$, R$_7$ and R$_8$ represent H or CH$_3$, g and h represent the number of repetitive units and both are integers not equal to 0, and i represents an integer of 1-4.

7. The ureteral stent according to claim 1, wherein the water-soluble polymerizable photosensitive monomer has a structure of general formula (I):

(I)

wherein: R$_1$=CH$_3$ or H; R$_2$ and R$_3$ are independently selected from linear alkyls having 1 to 20 C atoms or branched alkyls having 3 to 20 C atoms, respectively; X represents halogen; n=1-10; m=1-4; f=1-3; preferably, R$_2$ and R$_3$ are the same, X represents bromine, n=1, m=1, and f=1; and more preferably, R$_2$ and R$_3$ are both methyl or ethyl, X represents bromine, n=1, m=1, and f=1.

8. The ureteral stent according to claim 1, characterized in that,
the hydrophilic monomer comprises one or more of unsaturated carboxylic acid or carboxylate, unsaturated carboxylic ester, unsaturated acid hydroxyalkyl ester, unsaturated anhydride, unsaturated amide, unsaturated lactam and epoxyalkane; preferably, the hydrophilic monomer comprises one or more of (meth)acrylic acid, (meth)acrylamide, vinyl pyrrolidone, (meth)acrylate hydroxyethyl (propyl) ester, vinyl acetate, ethylene oxide, maleic acid, maleic anhydride, fumaric acid, fumaric anhydride and dimethylacrylamide; and more preferably, the hydrophilic monomer is selected from vinyl pyrrolidone.

9. The ureteral stent according to claim 1, wherein the molar concentration of the water-soluble polymerizable photosensitive monomer in the photocurable polymer is 0.08-12%, preferably 0.5-8%, further preferably 3-7.5%, more preferably 3-5%, and most preferably 4%.

10. A composite functional coating, comprising at least one pre-coating and at least one hydrophilic lubricating coating formed on the pre-coating,
wherein the pre-coating is formed by a pre-coated coating composition, the pre-coated coating composition comprises photocurable polyurethane, a polymerizable hydrophilic polymer and a solvent, the main chain of the photocurable polyurethane contains a tertiary amine group, the side chain thereof has an unsaturated double bond group and a photosensitive group unit, and the side chain of the polymerizable hydrophilic polymer has an unsaturated double bond group; and
the hydrophilic lubricating coating is formed by a hydrophilic lubricating coating composition, the hydrophilic lubricating coating composition comprises a photocurable polymer, the photocurable polymer is copolymerized by a water-soluble polymerizable photosensitive monomer and a hydrophilic monomer, the water-soluble polymerizable photosensitive monomer con- tains: 1) a unit containing a photosensitive structure; 2) a unit containing a quaternary ammonium salt structure; and 3) a unit containing an unsaturated bond structure; and the unit containing a photosensitive structure connected to the unit containing a quaternary ammonium salt structure at least through —C(=O)—, and the unit containing an unsaturated bond structure connected to the unit containing a photosensitive structure through the unit containing a quaternary ammonium salt structure.

11. The composite functional coating according to claim 10, wherein the mass concentration of the photocurable polyurethane in the pre-coated coating composition is 0.1-50%, preferably, the mass concentration is 0.5-30%, and more preferably, the mass concentration is 20-30%; and the mass concentration of the polymerizable hydrophilic polymer in the pre-coated coating composition is 0.1-30%, and preferably, the mass concentration is 1-20%; and the mass concentration of the photocurable polymer in the hydrophilic lubricating coating composition is 0.5-10%, preferably, the mass concentration is 2.5-7.5%, and more preferably 5%.

12. The composite functional coating according to claim 10, wherein the photocurable polyurethane is obtained at least by the reaction of a polypolyol, an unsaturated polyol containing a tertiary amine group, a polyol containing a benzophenone group, and isocyanate.

13. The composite functional coating according to claim 12, wherein the unsaturated polyol containing the tertiary amine group has the following structural formula:

wherein:
X represents —(CH$_2$)$_q$— or —CH(CH$_3$)CH$_2$—, q=1-3;
Y represents O or NH; and
Z represents H or CH$_3$.

14. The composite functional coating according to claim 10, wherein the structural formula of the photocurable polyurethane is as follows:

R represents the residue of polyol;
R$_1$ represents the residue of diisocyanate;
R$_2$ represents —(CH$_2$)$_p$—, p=1-4;
R$_3$ represents —(CH$_2$)$_q$—, q=1-3;
R$_4$ represents O or NH; R$_5$ represents H or CH$_3$; and
m, n, e, and f represent the number of repetitive units, and they are all integers not equal to zero.

15. The composite functional coating according to claim 10, wherein the structural formula of the polymerizable hydrophilic polymer is as follows:

wherein, R$_6$, R$_7$ and R$_8$ represent H or CH$_3$, g and h represent the number of repetitive units and both are integers not equal to 0, and i represents an integer of 1-4.

16. The composite functional coating according to claim 10, wherein the water-soluble polymerizable photosensitive monomer is obtained by performing acyl halogenation treatment on a molecular tail end of a compound containing a photosensitive structure, and then performing a reaction with (meth) acrylate containing a tertiary amino group.

17. The composite functional coating according to claim 10, wherein the water-soluble polymerizable photosensitive monomer has a structure of general formula (I):

wherein: $R_1$=$CH_3$ or H; $R_2$ and $R_3$ are independently selected from linear alkyls having 1 to 20 C atoms or branched alkyls having 3 to 20 C atoms, respectively; X represents halogen; n=1-10; m=1-4; f=1-3; preferably, $R_2$ and $R_3$ are the same, X represents bromine, n=1, m=1, and f=1; and more preferably, $R_2$ and $R_3$ are both methyl or ethyl, X represents bromine, n=1, m=1, and f=1.

18. The composite functional coating according to claim 10, wherein the molar concentration of the water-soluble polymerizable photosensitive monomer in the photocurable polymer is 0.08-12%, preferably 0.5-8%, further preferably 3-7.5%, more preferably 3-5%.

19. An article comprising a composite functional coating according to claim 10.

20. The article according to claim 19, wherein the article is a medical device.

* * * * *